United States Patent [19]
Oyama et al.

[11] Patent Number: 5,552,274
[45] Date of Patent: Sep. 3, 1996

[54] METHOD FOR DETECTING TARGET SEQUENCES BY OSCILLATION FREQUENCY

[75] Inventors: Noboru Oyama, Fuchu; Shuichiro Yamaguchi, Kanagawa-ken; Takeshi Shimomura, Kanagawa-ken; Keizaburo Miki, Kanagawa-ken, all of Japan

[73] Assignee: Terumo Kabushiki Kaisha, Tokyo, Japan

[21] Appl. No.: 117,329

[22] Filed: Sep. 7, 1993

[30] Foreign Application Priority Data

Sep. 7, 1992 [JP] Japan ................................. 4-238607
Feb. 19, 1993 [JP] Japan ................................. 5-029497

[51] Int. Cl.$^6$ ............................. C12Q 1/68; G01N 33/48
[52] U.S. Cl. ............................. 435/6; 436/94; 436/501; 422/68.1; 422/82.01
[58] Field of Search ................. 435/6; 436/94, 436/501; 422/68.1, 82.01; 935/78

[56] References Cited

U.S. PATENT DOCUMENTS

| | | | |
|---|---|---|---|
| 4,725,537 | 2/1988 | Fritsch et al. | 435/6 |
| 4,752,566 | 6/1988 | Collins et al. | 435/6 |
| 4,766,062 | 8/1988 | Diamond et al. | 435/6 |
| 4,818,680 | 4/1989 | Collins et al. | 435/6 |
| 4,847,193 | 11/1989 | Richards et al. | 435/6 |

FOREIGN PATENT DOCUMENTS

| | | |
|---|---|---|
| 295965 | 12/1988 | European Pat. Off. . |
| 3-54467 | 3/1991 | Japan . |
| 89/09938 | 10/1989 | WIPO . |

OTHER PUBLICATIONS

J. C. Andle et al., "An Acoustic Plate Mode Biosensor", *Sensors and Actuators*, vol. B8, No. 2, pp. 191–198, May 1992.

Y. Okahata et al., "Hybridization of Nucleic Acids Immobilized on a Quartz Crystal Microbalance", *J. Am. Chem. Soc.* vol. 114, pp. 8299–8300, 1992.

Richard C. Ebersole et al., "Amplified Mass Immunosorbent Assay with a Quartz Crystal Microbalance", *J. A. Chem. Soc.* vol. 110, pp. 8623–8628 (1988).

The Sangyou "Detection of Virus by the Use of Quartz Oscillator" (Laid Open Date: Aug. 4, 1992).

*Primary Examiner*—Kenneth R. Horlick
*Attorney, Agent, or Firm*—Burns, Doane, Swecker & Mathis, LLP

[57] ABSTRACT

Methods for detecting target DNA's in a sample on the basis of oscillation frequency using nucleic acid sequences immobilized to the surface of an electrode of an elastic wave element, and DNA sensors for conducting the methods are described. These methods provide for highly sensitive detection of target DNA's in a sample.

18 Claims, 15 Drawing Sheets

FIG. 3

First frequency measurement — Initial value setting

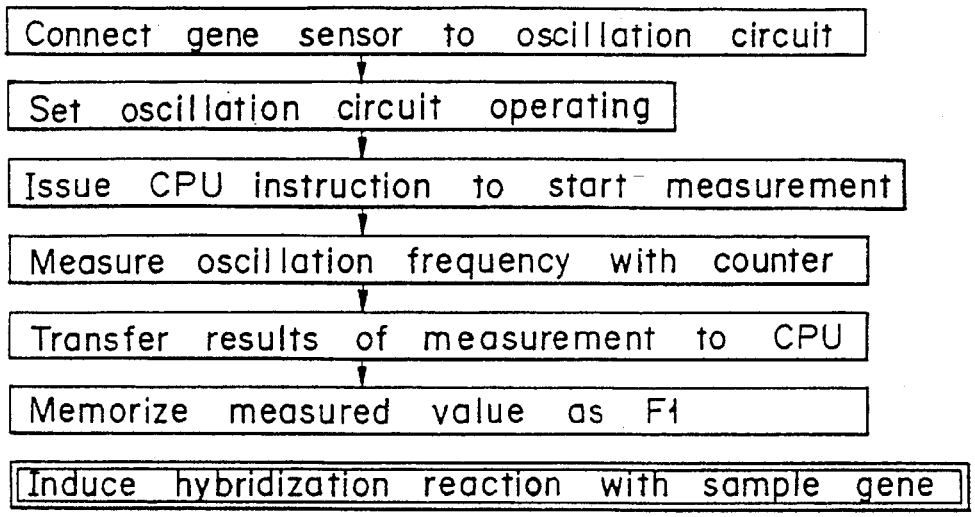

- Connect gene sensor to oscillation circuit
- Set oscillation circuit operating
- Issue CPU instruction to start measurement
- Measure oscillation frequency with counter
- Transfer results of measurement to CPU
- Memorize measured value as F1
- Induce hybridization reaction with sample gene

Second frequency measurement — Gene measurement

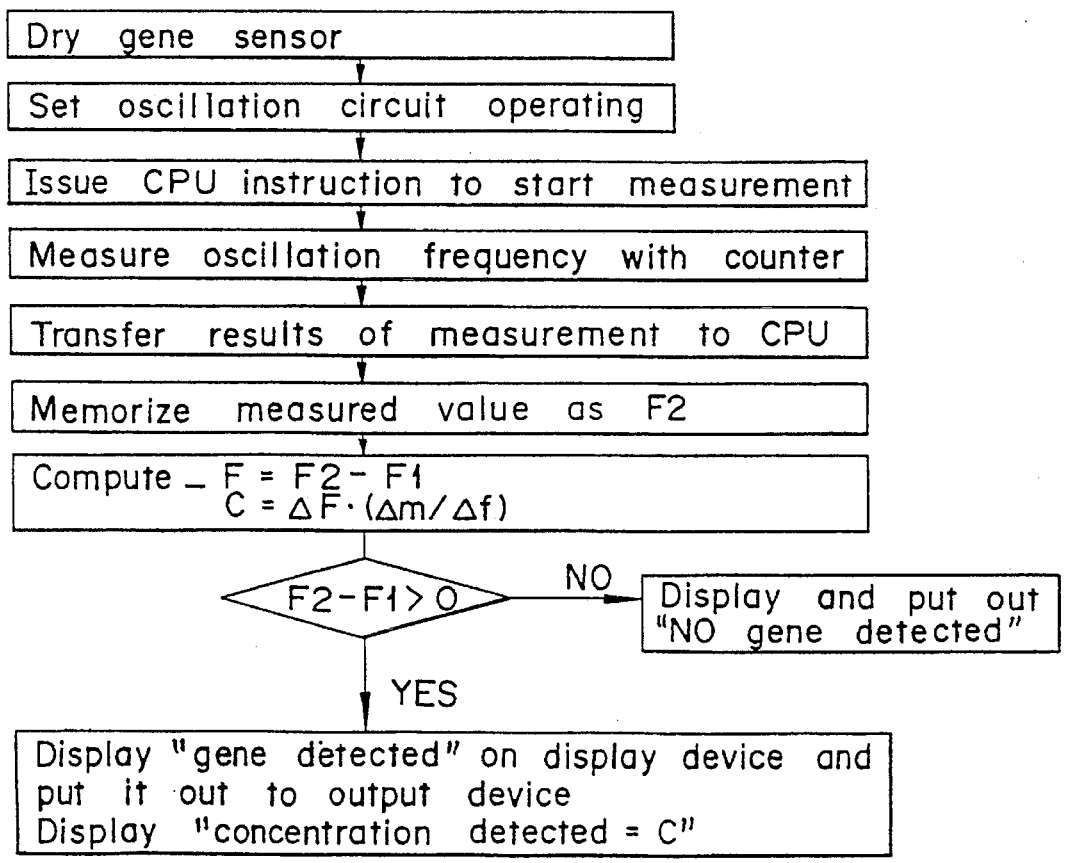

- Dry gene sensor
- Set oscillation circuit operating
- Issue CPU instruction to start measurement
- Measure oscillation frequency with counter
- Transfer results of measurement to CPU
- Memorize measured value as F2
- Compute $\Delta F = F2 - F1$
  $C = \Delta F \cdot (\Delta m / \Delta f)$ Decision: $F2 - F1 > 0$

- NO → Display and put out "NO gene detected"
- YES → Display "gene detected" on display device and put it out to output device. Display "concentration detected = C"

FIG. 5(A)

First frequency measurement  Initial value setting

| Connect sensor to analyzer |

| Transfer parameter value for measurement from CPU to analyzer Issue instruction to start impedance measurement |

| Determine relation between admittance and frequency |

| Transfer results of measurement to CPU |

| Analyze relation between admittance and frequency Estimate resonance frequency and resonance resistance |

| Memorize resonance frequency as F1 |

| Induce hybridization reaction with specimen |

Second frequency measurement  Gene measurement

| Transfer parameter value for measurement from CPU to analyzer Issue instruction to start impedance measurement |

| Determine relation between admittance and frequency |

| Transfer results of measurement to CPU |

| Analyze relation between admittance and frequence Estimate resonance frequency and resonance resistance |

| Memorize resonance frequency as F2 |

Compute $\Delta F = (F2 - F1)$
$C = \Delta F \cdot (\Delta m / \Delta f)$ $F2 - F1 > 0$ ?
NO → Display and put out "NO gene detected"

YES ↓

Display "gene detected" on display device and put it out to output device
Display and put out concentration detected = C Reaction of hybridization with sample gene

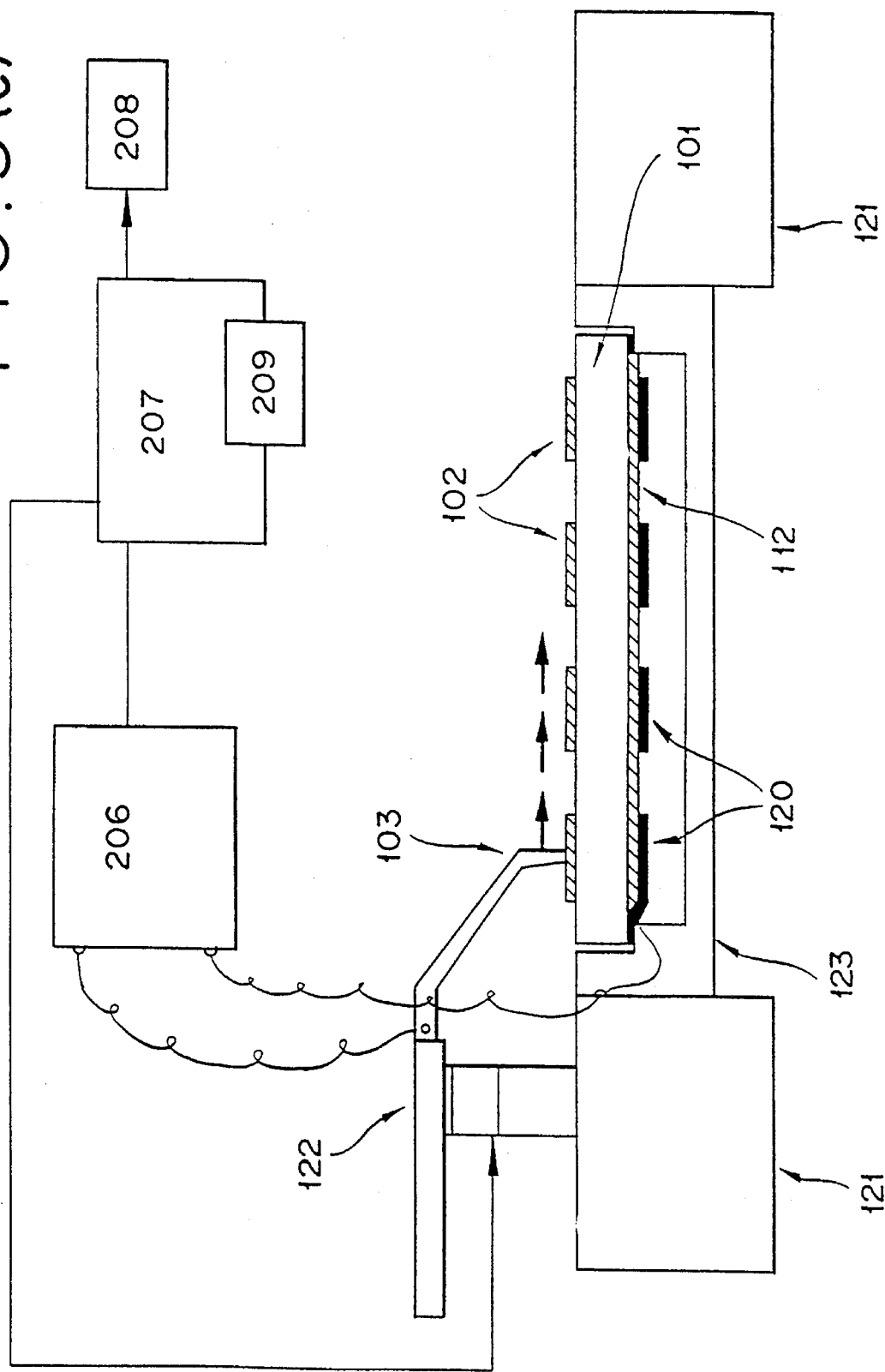

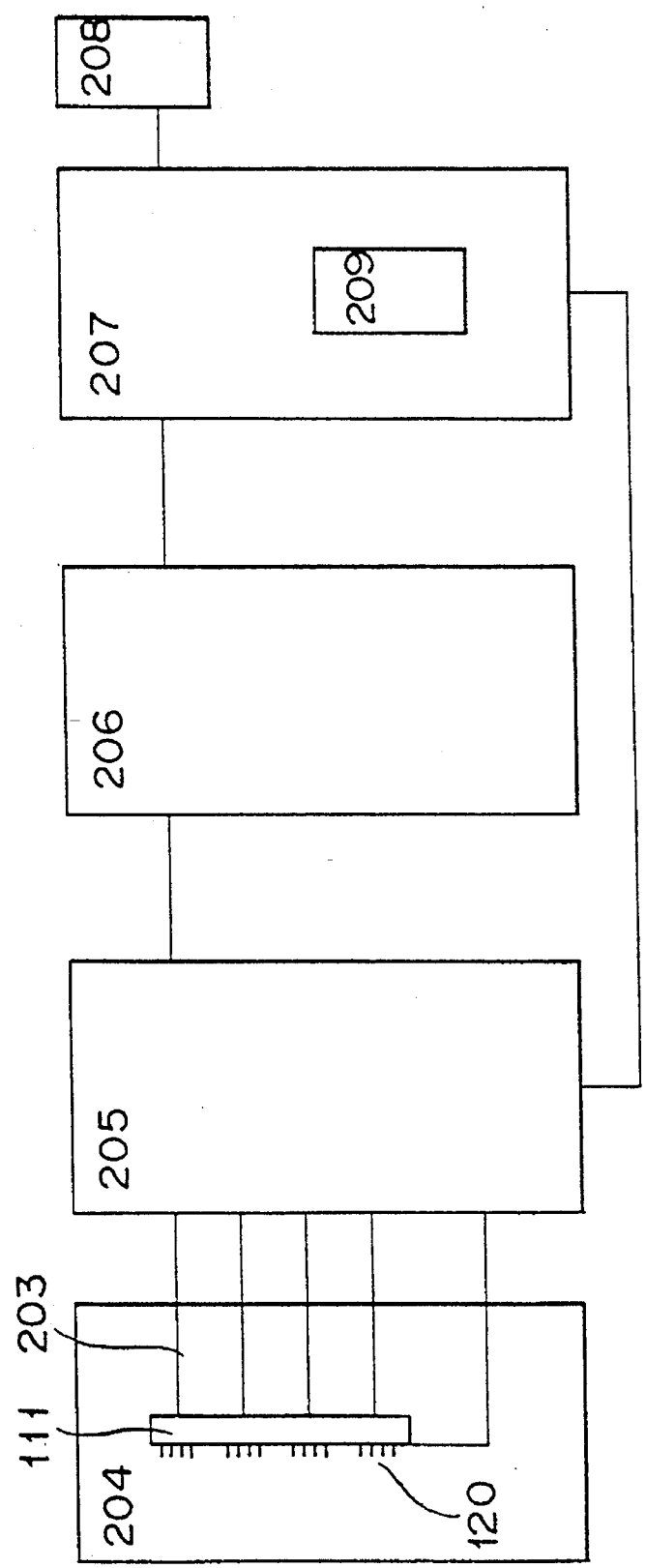

Flow chart of operation of sequence reading device (1) Measurement of initial value of sensor

FIG. 11(B)

(2) Hybridization

| Induce hybridization reaction with sample | By the same method as in FIG. 5 (B)

FIG. 11(C)

(3) Determination of DNA

```
Set sensor 10 on probe 4
Make minute probe 3 to contact minute electrode 2
          ↓
    Start measurement
          ↓
       Initialize                  Initialize device for
                                   transmitting parameter
                                   to impedance measuring
                                   device
          ↓
FOR n = 0 TO 255
   ↑
   │  FOR m = 0 TO 255
   │     ↑         ↓ (Set measurement addresses (m,n))
   │     │  Transmit measurement addresses (m,n) to scanner 5
   │     │         ↓
   │     │  Electrically connect to minute electrodes at the
   │     │  addresses (m,n)
   │     │         ↓
   │     │  Issue instruction to start measurement of impedance
   │     │         ↓
   │     │  Determine relation between admittance and frequency
   │     │         ↓
   │     │  Transmit results of measurement to computer
   │     │         ↓
   │     │  Analyze relation between admittance and frequency
   │     │  Estimate resonance frequency and resonance resistance
   │     │         ↓
   │     │  Memorize resonance frequency as two-dimensional
   │     │  sequence variables F2 (m,n) in memory device 31
   │     │         ↓
   │     NEXT m
   │
   NEXT n
          ↓                    (Increment address numbers)
```

(4) Reading of base sequence

FIG. 12

Experiment 1
DNA's having 20 bases in the known sequence (Formula 1) were synthesized and tested by the use of a gene reading device manufactured in Example 1. (x,y) denotes addresses

..... (1)

| | GGATCGATCCAATCGTACTG | | | GTCATGCTAACCTAGG | |
|---|---|---|---|---|---|
| 1 | GGATCGAT | (99,163) | 1' | TAGCTAGG | (202,201) |
| 2 | GATCGATC | (14,141) | 2' | CTAGCTAG | (144,144) |
| 3 | ATCGATCC | (53,54) | 3' | CCTAGCTA | (156,92) |
| 4 | TCGATCCA | (212,216) | 4' | ACCTAGCT | (39,23) |
| 5 | CGATCCAA | (80,99) | 5' | AACCTAGC | (201,5) |
| 6 | GATCCAAT | (67,141) | 6' | TAACCTAG | (114,193) |
| 7 | ATCCAATC | (13,53) | 7' | CTAACCTA | (92,112) |
| 8 | TCCAATCG | (54,212) | 8' | GCTAACCT | (23,156) |
| 9 | CCAATCGT | (219,80) | 9' | TGCTAACC | (5,231) |
| 10 | CAATCGTA | (108,67) | 10' | ATGCTAAC | (193,57) |
| 11 | AATCGTAC | (177,13) | 11' | CATGCTAA | (112,78) |
| 12 | ATCGTACT | (199,54) | 12' | TCATGCTA | (156,211) |
| 13 | TCGTACTG | (30,219) | 13' | GTCATGCT | (231,180) |
| R | GGATCGATCCAATCGTACTG | | R | GTCATGCTAACCTAGG | |

| | CCGAGCTAGGTTAGCATGAC | | | CAGTACGATTGGATCGAGCC | |
|---|---|---|---|---|---|
| 14 | CCGAGCTA | (156,88) | 14' | ATCGAGCC | (37,54) |
| 15 | CGAGCTAG | (144,98) | 15' | GATCGAGC | (137,141) |
| 16 | GAGCTAGG | (202,137) | 16' | GGATCGAG | (98,163) |
| 17 | AGCTAGGT | (42,39) | 17' | TGGATCGA | (216,232) |
| 18 | GCTAGGTT | (175,156) | 18' | TTGGATCG | (54,250) |
| 19 | CTAGGTTA | (188,114) | 19' | ATTGGATC | (141,62) |
| 20 | TAGGTTAG | (242,202) | 20' | GATTGGAT | (163,143) |
| 21 | AGGTTAGC | (201,43) | 21' | CGATTGGA | (232,99) |
| 22 | GGTTAGCA | (36,175) | 22' | ACGATTGG | (250,24) |
| 23 | GTTAGCAT | (147,188) | 23' | TACGATTG | (62,198) |
| 24 | TTAGCATG | (78,242) | 24' | GTACGATT | (143,177) |
| 25 | TAGCATGA | (56,201) | 25' | AGTACGAT | (99,44) |
| 26 | AGCATGAC | (225,36) | 26' | CAGTACGA | (24,75) |
| R | CCGAGCTAGGTTAGCATGAC | | R | CAGTACGATTGGATCGAGCC | |

METHOD FOR DETECTING TARGET SEQUENCES BY OSCILLATION FREQUENCY

BACKGROUND OF THE INVENTION

1. Field of the Invention

This invention relates to a method for determination of DNA and a sensor therefor. More particularly, it provides a method for detection of DNA which permits the detection to be performed expeditiously with a simple procedure and also provides a sensor to be used for such determination.

2. Description of the Prior Art (1) General methods of testing for DNA:

Prior to the present invention, various means for DNA testing and DNA diagnosis have been disclosed, including, e.g., dot blot methods, in situ hybridization methods, Southern blotting methods, PCR methods, and polygonal DNA marker methods, However, all of such methods have problems. For example, the dot blot method and the in situ hybridization method have problems of poor sensitivity of detection, although they are advantageous in the fact they are relatively simple and require little time for DNA detection. By contrast, Southern blotting methods provide high sensitivity of detection, but are complicated and time-consuming. Means of DNA analysis which obviates some methods associated with DNA testing and DNA diagnosis, are the Sanger methods and the Maxam methods of DNA detection. However, such methods are still disadvantageous because it is difficult to obtain ideal analysis of DNA which is composed of more than 1,000 base pairs.

F. Sanger et al have published in Proc. Natl. Acad. Sci., USA 74, 5463 (1977) a method for identifying a base sequence in a given DNA by using a reaction for extracting one of the four precursor nucleotides and a reaction for incorporating one precursor nucleotide therein.

A. Maxam and W. Gilbert have published in Proc. Natl. Acad. Sci., USA 74, 560 (1977) a method for sequencing a base sequence contained in a given DNA by labeling the 5'-terminal of the DNA with $^{32}P$, reacting said DNA with a chemical reagent, thereby inducing partial decomposition of the DNA to its bases, and the formation of DNA fragments differing in length, and fractionating the DNA fragments by electrophoresis. However, this method requires that the terminal labeled pure DNA be available in a large amount, therefore it requires amplification of the DNA by cloning, by PCR or by LCR. Thus, this method is time-consuming and costly.

The PCR method features unusually high sensitivity because it is adapted to effect propagation of the DNA at the target site to 100,000 to 1,000,000 times the original size. It, however, is subject to contamination and complicated operating conditions.

Conventional apparatuses for DNA testing are subject to various problems including consumption of an unduly long time, requirement of special test room conditions because of required use of radiation, and need for means of disposal of hazardous spent isotopes. Thus, there is a substantial need for the development of a DNA sensor which provides for high sensitivity but which does not require use of an isotope.

(2) QCM

Successful use of a quartz crystal microbalance (QCM) for DNA assay has been disclosed to the art. This device comprises a quartz plate and electrodes formed on each of the opposite surfaces of the quartz plate. These two electrodes are connected to external oscillating circuits and are adapted to resonate with the frequency inherent in the quartz plates. This frequency is related to the mass of quartz as well as the mass, viscosity, and viscoelasticity of the electrodes which are in contact with the quartz. Generally, the variation of resonant frequency and that of mass of a substance in contact with quartz are correlated. Assuming that the layer and/or substance in contact with quartz behaves as a rigid body, the variation of mass may be calculated in accordance with the Sauerbrey formula [G. Z. Sauerbrey, Z. Phys., 155 (1959) 206] shown below.

$$\Delta f = 2f_0^2 \Delta m/A(\rho_q \mu_q)^{1/2} \quad (1)$$

wherein $\Delta f$ is a shift of frequency, $f_0$ is fundamental frequency of quartz, $\Delta m$ is a variation of mass, A is a available surface area of an electrode, $\rho_q$ is a density of quartz (2.648 g cm$^{-3}$), $\mu_q$ is a constant of shift vibration (which is 2.947×10$^{11}$ dynes cm$^{-2}$ in the case of AT cut crystal).

R. C. Ebersole and M. D. Ward have disclosed in U.S. Pat. No. 4,999,284 and in J. Amer. Chem. Soc., (1988), 110, 8623–8628 a method which provides for detection determination of an immune substance with high sensitivity which comprises immobilizing the immune substance on a quartz oscillator. These publications touch on DNA but fail to show a concrete procedure.

J. C. Andle et al. have reported in Sensors and Actuators B. 8 (1991) 191–198 the successful detection of DNA by the use of a sensor comprising a so-called SAW device having a comb electrode formed on the surface of a piezoelectric plate. In their report, the sensitivity of DNA detection is indicated to be 0.1 nanogram in mass sensitivity at a phase of 0.5°.

In J. Amer. Chem. Soc., (1992), 118, 8299–8300, Y. Okahata et al. have disclosed a method which allows for the detection of a variation of weight of a given oligonucleotide due to hybridization by immobilizing 10mer of a SH Group-modified sample of the oligonucleotide on the surface of a gold electrode of a quartz oscillator, exciting the quartz so as to induce oscillation, measuring the variation of resonance frequency generated by the oscillation, and calculating the magnitude of the variation of weight based on the variation of the resonant frequency.

These methods provide for both DNA detection and quantitative measurement of test DNA in a sample on the basis of the variation in resonance frequency. For practical use in DNA diagnosis and testing, however, the method must warrant sensitivity of not less than 10$^{-16}$ mol. The methods cited above provide DNA detection sensitivity on the order of 0.1 to 1 nanogram. They, therefore, have a problem of impracticability due to unduly low sensitivity. Ideally, a method should enable detection of a single DNA. Thus, the development of a method and apparatus which allows for detection of a single DNA is needed. Even assuming a sample DNA to be detected is large, e.g. a DNA having a molecular weight of 10$^9$ such as a human gene, it still cannot be detected using conventional methods because the mass per molecule is 1.7×10$^{-15}$ (10$^9$/6.02×10$^{23}$) g.

Moreover, the method proposed by Okahata et al. is not fully reliable because it must rely on aspiration for immobilization of DNA. Thus, it is subject to inaccurate determination of DNA.

An object of this invention, therefore is to provide a novel method for determination of DNA and a sensor to be used therefor.

Another object of this invention is to provide a DNA sensor which is formed of an elastic wave element which is so supersensitive that it allows for the immobilization of a modified DNA which enables detection of a single DNA and to provide a method for the determination of DNA using this DNA sensor.

Yet another object of this invention is to provide a base sequence reading apparatus which permits highly sensitive detection or isolation of DNA and which allows highly accurate detection of a base sequence in the DNA for DNA sequence analysis.

SUMMARY OF THE INVENTION

The objects described above are accomplished by a method for determination of DNA, which method comprises immobilizing the 5'-terminal of a nucleotide chain on one side of the DNA to the surface of an electrode of an elastic wave element and further immobilizing a chemical species on the 5'-terminal of a nucleotide chain on the opposite side of the DNA to which the nucleotide chain is hybridized thereby forming a DNA sensor and then detecting an increase in the frequency of oscillation based on a decrease in the mass to be exchanged for and hybridized to the target DNA thereby effecting detection and determination of the DNA.

These objects are further accomplished by a DNA sensor which is composed of an elastic wave element and a nucleotide having a nucleic acid sequence identical with that of a DNA which is to be detected and which has a nucleotide chain on one side immobilized on the surface of an electrode of the elastic wave element and has a chemical species of a mass larger than that of the DNA under test immobilized on a nucleotide chain on the opposite side to which the nucleotide chain is hybridized.

The term "elastic wave element" as used in this invention refers to an electroacustic transducer and shall be construed herein as indicating a quartz oscillator, a surface elastic wave element, or a similar device.

This invention contemplates a method for the determination of a DNA and a DNA sensor, wherein the chemical species has a mass in the range of 0.01 pg to 1 ng. It also contemplates a method for the determination of a DNA and a DNA sensor, wherein the chemical species has a specific gravity of not less than 1 g/cm$^3$. It further contemplates a method for the determination of a DNA and a DNA sensor, wherein the chemical species has a diameter in the range of 0.01 to 10 µm. It contemplates a method for the determination of a DNA and a DNA sensor, wherein the chemical species is at least one member selected from the group consisting of synthetic resins, magnetic substances, metals, and metal oxides. This invention also contemplates a method for the determination of a DNA and a DNA sensor, wherein the material of the chemical species is polystyrene or a fluorine resin. It also contemplates a method for the determination of a DNA and a DNA sensor, wherein the material of the chemical species is gold or titanium oxide. It further contemplates a method for the determination of a DNA and a DNA sensor, wherein the material of the chemical species is a ferrite. Further, it contemplates a method for the determination of a DNA and a DNA sensor, wherein the chemical species is made of a material having an adsorbing capacity too small to induce either nonspecific adsorption of proteins or nucleic acids other than the DNA which is to be tested for or aggregation of particles themselves.

The objects described above are accomplished further by a base sequence reading device which comprises an electromechanical conversion element, a plurality of nucleotide chains of known base sequence immobilized to an electrode on the obverse surface of the electromechanical conversion element, microelectrodes disposed on the reverse surface of the electromechanical conversion element so as to correspond to the nucleotide chains, means for measuring a change in the electric property of the aforementioned electromechanical element connected to the microelectrodes, and processing means for reading a base sequence of the gene being tested for in accordance with the base sequence of the nucleotide chain corresponding to the microelectrode in which the measurement of the change has been made.

This invention contemplates a base sequence reading device, wherein the plurality of nucleotide chains are composed of 7 to 100 bases. It further contemplates a base sequence reading device, wherein the plurality of nucleotide chains have one equal chain length (N-mer). It also contemplates a base sequence reading device, wherein the plurality of nucleotide chains as the N-mer constitute a total sequence library for the N-mer. It also contemplates a base sequence reading device, wherein the plurality of nucleotide chains are a fragment of a base sequence predicted to be contained in the gene which is to be detected. It further contemplates a base sequence reading device, wherein the nucleotide chain has another nucleotide chain hybridized thereto and the other nucleotide chain has immobilized thereon a chemical species having a mass greater than the gene which is to be detected. It contemplates a base sequence reading device, wherein the chemical species comprise minute particles of at least one member selected from the group consisting of polystyrene and magnetic substances. It also contemplates a base sequence reading device, wherein the electromechanical conversion element is an elastic wave element. Further, it contemplates a base sequence reading device, wherein the elastic wave element is a quartz oscillator (QCM) or a surface elastic wave element (SAW).

Therefore, the method of the present invention for the determination of a DNA and the DNA sensor used in this method are based on the principle that when a substance having a mass larger than that of the DNA under test is immobilized on a sensor in advance of the test, the DNA which is being tested for displaces the immobilized substance and binds to the sensor thereby resulting in a mass decrease. Thus, the DNA sensor exhibits high sensitivity and high selectivity in avoiding the adsorption of a nonspecific substance. Further, this invention permits simple and safe handling because it does not use radioactive labels or enzymes. Moreover, it operates conveniently. It also allows quick determination compared conventional DNA detection methods. Since this invention, based on knowledge of part of the base sequence of the DNA which is being tested for, allows for the detection of a gene with high sensitivity, it can detect HIV virus, HCV virus, etc. on the DNA level and, therefore, can be used for diagnosis and therapy of diseases whose causes are related to specific DNAs.

Since the detecting part of the DNA sensor of this invention may be regenerated, the DNA sensor can be used repeatedly which lowers the cost of testing. Moreover, a plurality of DNA sensors of this invention may be arrayed and utilized for performing many types of test simultaneously.

The base sequence reading device of the present invention provides for simple handling because it does not use radioactive labels or enzymes. Owing to the simplicity of the operation, the method of this invention allows the determination to be performed quickly as compared with conventional methods. Since the detecting part of the DNA sensor of this invention is regenerable, the DNA sensor can be used repeatedly and the cost of testing is lowered. Since the gene reading device of the present invention has a plurality of peptide chains immobilized therein, it can be utilized for performing many kinds of tests simultaneously. This invention excels in both selectivity (specificity) and sensitivity because it operates on the principle of detecting a decrease in mass. This is contrary to conventional methods. Then from the medical point of view, this invention expedites the elucidation of human genes, contributes to the diagnosis of diseases whose causes are genetic and the therapy of intractable diseases, and serves to promote the welfare of mankind. Since it can efficiently elucidate cancer genes and cancer depressing genes, it widens the range of measures available for preventing occurrence or recurrence of the disease. Further, this invention allows precise and quick diagnosis of infectious diseases such as caused by HIV virus and HCV virus by genetic detection and consequently permits administration of radical therapies in early stages of diseases.

BRIEF DESCRIPTION OF THE DRAWINGS

FIG. 3 is a flow chart of the operation of the detection system shown in FIG. 2.

FIG. 9(C) is a concept illustrating another embodiment of a probe device.

FIG. 10 is a block diagram illustrating one mode of embodying a base sequence reading system according to the invention.

FIG. 11(A) to(D) are flow charts of the operation of the system illustrated in FIG. 10.

FIG. 12 is a diagram illustrating one example of a base sequence read using the base sequence reading device according to the invention using SEQ ID NOS. 5 and 7–9.

PREFERRED EMBODIMENT OF THE INVENTION

According to this invention, the difference in variation of mass which is generated when a gene DNA subjected to detection homologously displaces a modified DNA comprising the same sequence as the DNA which is to be detected and which is immobilized on a sensor is measured in the form of a variation of vibration of the elastic wave element with high sensitivity. Thereby, the detection and identification of the gene being used on the level of one unit can be carried out expeditiously and easily by setting the mass of the modified DNA to be substituted at a value greater than that of the DNA which is being detected, preferably at a value greater than the limit of detection.

The dissociation of a two-chain DNA may be accelerated by elevating the temperature of the solution (to about 100° C.) and/or by increasing the concentration of an electrolyte and using a dissociation solution.

When a DNA (B) chain complimentarily bound to a DNA (A) chain which is immobilized on the QCE is homologously exchanged for a sample DNA chain, it is released together with a chemical species bound to the DNA (B) chain. At this time, the variation of mass (=x) equivalent to (sample DNA (B) chain—high-mass chemical species—complimentarily bonded DNA (B) chain) results. In the absence of the high-mass chemical species, the variation of mass (=v) which results is equivalent to (sample DNA chain—complimentarily bonded DNA (B) chain).

When the mass of the high-mass chemical species is sufficiently larger than that of the sample DNA chain, the variation of mass is amplified (x/y) times as triggered by the chemical variation (homologous exchange reaction of DNA). In this sense, the use of the term "chemical amplification" may be justified. It is seen that the detection of one piece of DNA can be attained by using an immobilization grade chemical species having a mass of not less than 1 pg and, at the same time, using a quartz oscillator whose mass detection limit is not less than 1 pg. Irrespective of whether the DNA under test is one base pair having a molecular weight of 660 or a very large DNA molecule having a molecular weight of $10^9$, it can be detected with the QCM because the DNA being tested for, on displacing the immobilized DNA, gives rise to a variation of not less than 1 pg. The increase or decrease of mass of the DNA which results in this case from the displacement involving the DNA being tested for can be ignored. The sensor's response to the question as to how many pieces of DNA having a chemical species bound to the sensor surface have been released is displayed in the form of a digital variation. In other words, the variation of mass caused in this case is amplified from $10^3$ to $10^9$ times.

Figure 1:
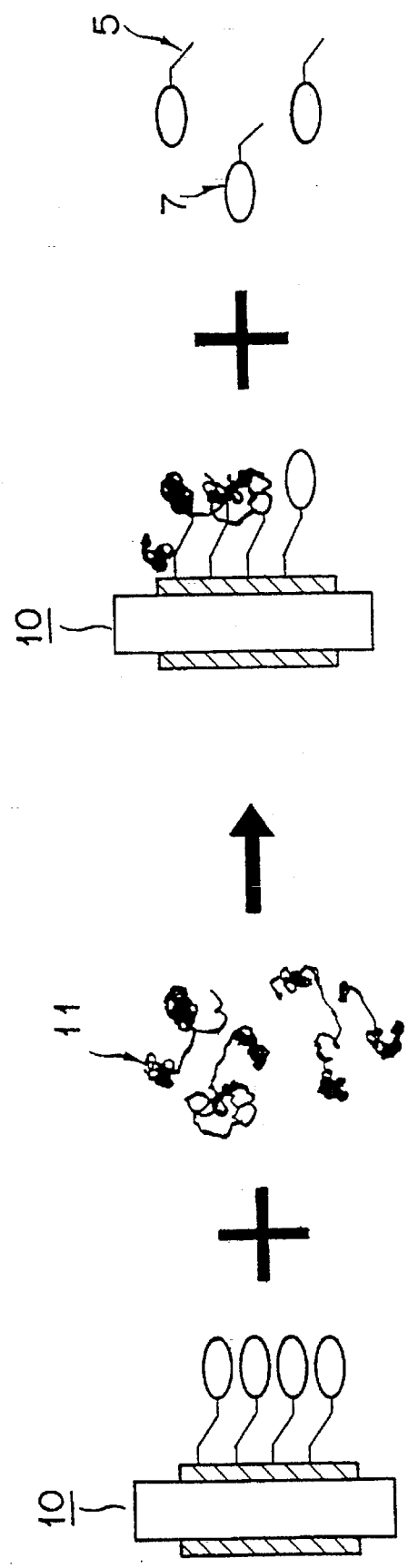
FIG. 1 is a diagram depicting the principle of DNA detection according to the invention.

The gene sensor 10 of this invention which is obtained as described above allows for the detection of a gene as follows (FIG. 1). A liquid specimen containing the DNA which is to be detected is placed in contact with the gene sensor 10. For the purpose of facilitating the bond of a gene 11 being detected, the hydrogen bond responsible for the formation of a complementary union may be weakened by application of heat and/or addition of an electrolyte. This treatment breaks the complementary union of a nucleotide column and the gene 11 being detected. Then, the anneal effected by gradual fall of temperature induces displacement of the gene 11 being detected with a nucleotide chain 5' modified with a modifying substance 7 and causes attachment of the gene 11 to the surface of an electrode 3 of a quartz oscillator 1.

As a result, the mass of the electrode 3 decreases and the frequency of oscillation of the quartz oscillator 1 increases. This increase of frequency clearly denotes the presence of the gene 11 in the liquid specimen. Adsorption of a nonspecific substance to the surface of the electrode 3 occurs at the same time and this adsorption operates in the direction of lowering the frequency of oscillation. The gene sensor 10 of this invention, therefore, provides for very high selectivity.

Figure 2:
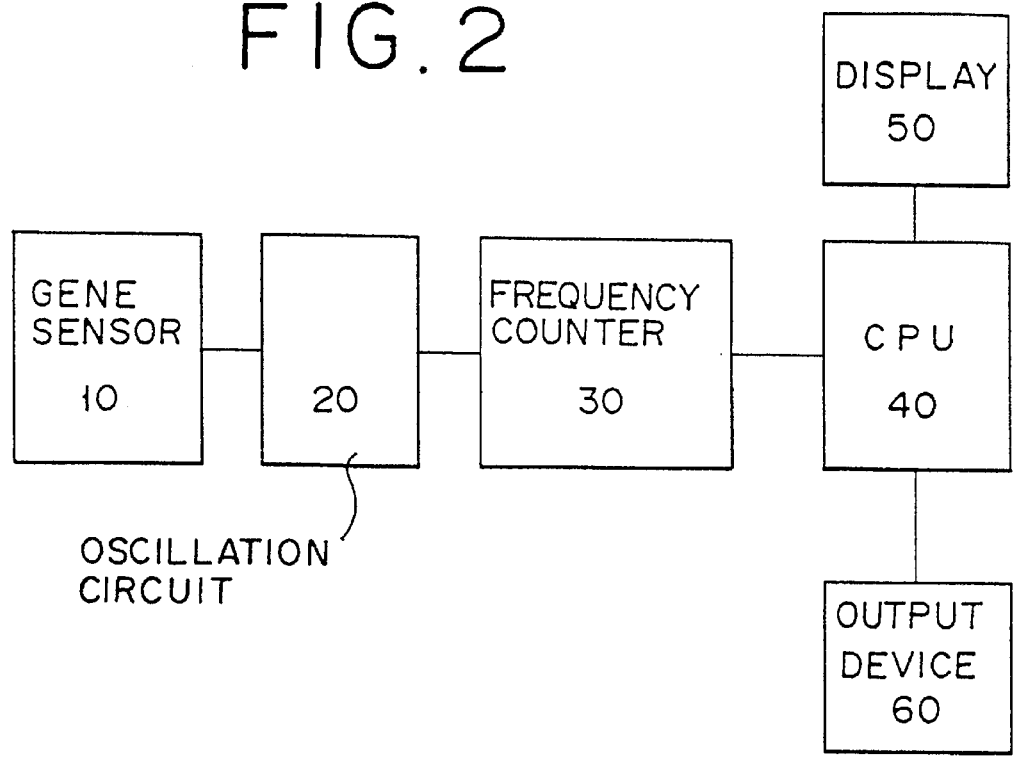
FIG. 2 is a structural diagram of a DNA detection system incorporating therein the DNA sensor according to the invention.

The increase of the frequency of oscillation of the quartz oscillator 1 is detected by a measuring system constructed as illustrated in FIG. 2 and adapted to display or put out the result of the measurement. The quartz oscillator 1, on being connected to an oscillation circuit 20, oscillates at a (resonance) frequency which is inherent in the quartz oscillator. The frequency of oscillation is amplified by the oscillation circuit 20. A frequency counter 30 computes this frequency and transmits it to a computer. Then, the computer compares the magnitudes of resonance frequency before and after the DNA detection procedure to determine any variation of the frequency and, based on the data of frequency increase, decides whether the gene of interest is present. The concentration or content of the gene in the liquid specimen can be computed with reference to a calibration curve which curve is based on the known size of variation of the resonance frequency. The result of this measurement is transmitted to a display device 50 or an output device 60 to be displayed or printed out by the device.

The flow chart of the operation described above is given in FIG. 3. In this diagram, the term ($\Delta m/\Delta f$) denotes the mass sensitivity determined in advance.

Figure 4:
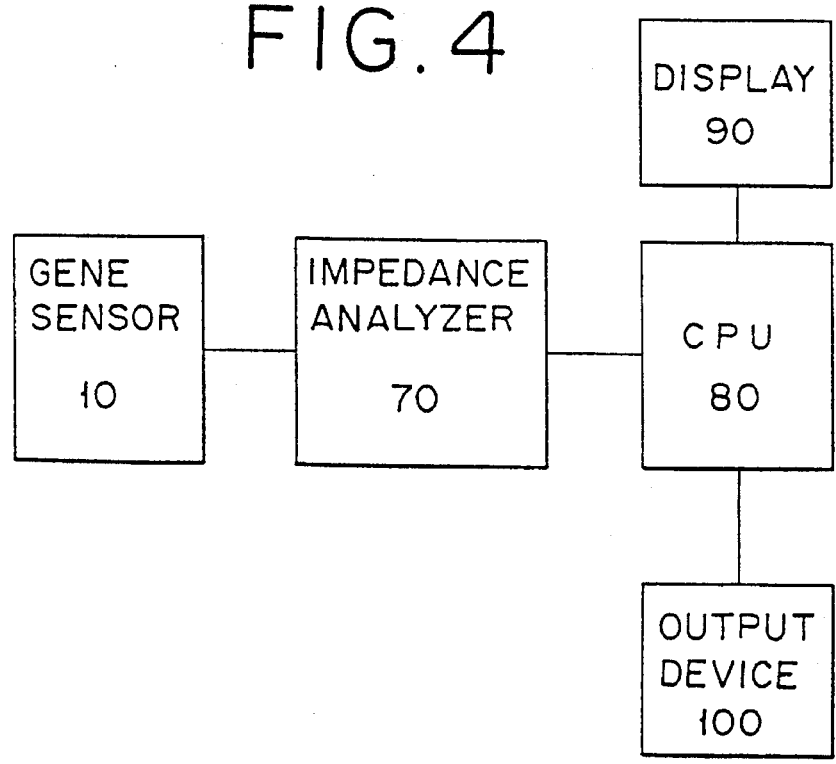
FIG. 4 is an explanatory diagram illustrating another mode of embodying the DNA determining system according to the invention.

The surface area of the electrode may be minimized to enhance the mass sensitivity of the quartz oscillator 1 (as shown by Formula 1). A decrease in the surface area, however, requires an increase in the electrode resistance. If the increased electrode resistance happens to surpass the magnitude of negative resistance of the oscillation circuit, the measurement by the oscillation method is no longer feasible. When the oscillation method fails, a measuring system constructed as illustrated in FIG. 4 is used. The dependency of the admittance of the quartz oscillator 1 upon frequency is measured by the use of an impedance measuring device 70. The results of this measurement are transmitted to a computer 80. The presence of the target gene can be determined and the identification of the gene can be accomplished as described above because the resonance frequency can be computed based on the fact that the frequency at which the conductance maximizes the frequency spectrum of admittance results in the resonance frequency.

Figure 5B:
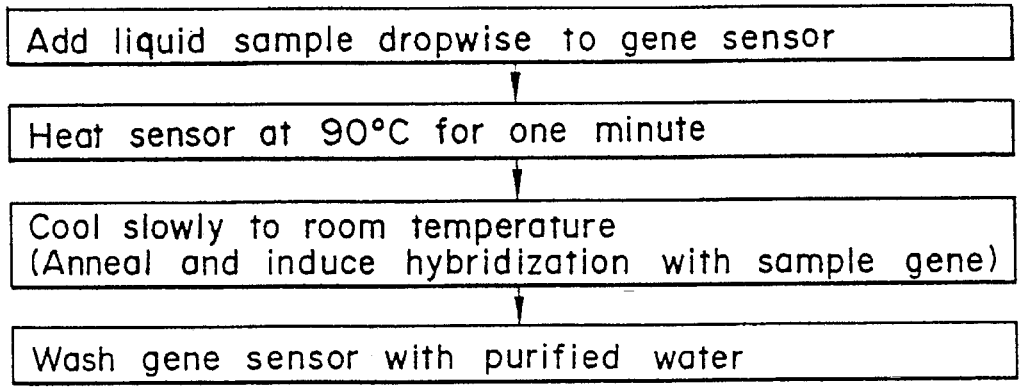
FIG. 5(A) and(B) are flow charts of the operation of the detection system illustrated in FIG. 4.

The flow chart of the operation described above is shown in FIG. 5(A) and FIG. 5(B).

EXAMPLE 1

Figure 6:
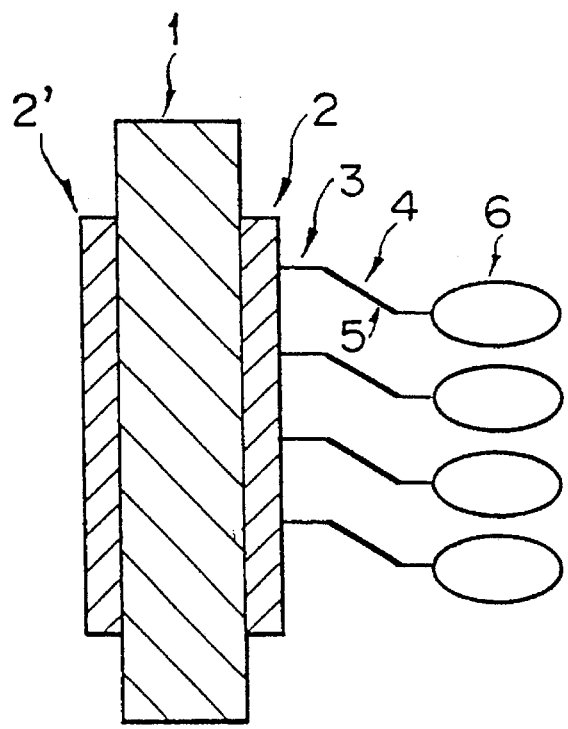
FIG. 6 is a model diagram illustrating a first embodiment of the DNA sensor according with this invention.

FIG. 6 illustrates the construction of a DNA sensor of a first embodiment of the invention.

Gold disc electrodes 2, 2' for exciting oscillation were formed one each on the opposite surfaces of the quartz substrate 1. The quartz oscillation substrate 1 was formed of an AT cut quartz disc measuring 12 mm in diameter and 0.33 mm in thickness. The gold electrodes were formed by the use of a high frequency sputter device (produced by Nichiden Anelba K. K. and marketed under product code of "SPF-210H").

The surface of the gold electrode 2 is coated with a saline coupling agent 3 (τ-glycidoxypropyl saline, produced by Toray-Dow Corning Silicone K. K. and marketed under product code of "SH6040"). The quartz substrate 1 and a container holding the saline coupling agent were placed together in a vacuum chamber, left standing therein under a vacuum for two hours to permit adsorption, and then allowed to react for 30 minutes at ambient pressure at 150° C.

DNA's 4 and 5 were immobilized on the surface of the gold electrode 2. The saline compound had the OH group thereof activated by use of water-soluble carbodiimide and then was allowed to react at least partly with a DNA having the same sequence as the DNA to be detected. The resultant ester bondage of the phosphoric acid at the 5'-terminal of DNA with the OH group of the saline coupling agent immobilized one of the two chains of the DNA on the surface of the quartz substrate.

To the 5'-terminal of a DNA chain 5 bound to the substrate on the opposite side, minute particles 6 of polystyrene were similarly immobilized. The minute polystyrene particles [produced by Polyscience Corp. and marketed under trademark designation of "Polybeads (Microsphere)"] comprise an average mass of about 1 pg. Several OH groups were introduced into each of the minute polystyrene particles. The DNA and the minute polystyrene particles (PS) immobilized on the quartz substrate were treated with water-soluble carbodiimide to provide for ester bonding between the phosphoric acid group of the DNA (B) chain with the OH group of the minute polystyrene particles. As a result, a DNA sensor 10 of the construction of QCE-DNA (A)/DNA (B)-PS.

The DNA sensor 10 thus produced was tested under a blanket of dry air for oscillation frequency. The basic oscillation frequency was 5,002,201 Hz. When the QCE, after having DNA-PS immobilized on the surface thereof, was tested for oscillation frequency under dry air, the result was 5,001.906 Hz. By determining the relation between the resonance frequency and the mass in advance of test, the mass sensitivity was found to be 3.4 ng/Hz, a value closely approximating closely the theoretical value. The amount of DNA-PS immobilized, therefore, was found to be $(5001906-5002201)\times(-3.4)=1,000$ [ng]. The fact that the minute polystyrene particles used herein had an average mass of 1 pg indicates that about $10^6$ sets of DNA-PS had been immobilized.

The DNA sensor 10 was exposed to contact with 100 μl of a liquid specimen containing the DNA subjected to detection in a total amount of $1\times10^5$ molecules, left standing therein at a liquid temperature of 93° C. for one minute, and annealed by slowly lowering the liquid temperature. When the DNA sensor 10 was cleaned and tested in dry air for oscillation frequency, this frequency was 5,001.936 Hz. The results indicate that the frequency was increased by 30 Hz and the DNA (B)-PS whose mass was $30\times(-3.4)=102$ ng was released. This mass, as reduced to the number of molecules of DNA (B)-PS, equals $1.02\times10^5$, indicating that the complementary exchange reaction occurred substantially quantitatively. The limit of detection of the DNA sensor configured as described in Example 1, in the determination of frequency with accuracy of 1 Hz, was about 3,000 molecules of DNA.

TABLE 1

| Number of molecules of sample DNA | Variation of oscillation frequency |
|---|---|
| $5 \times 10^5$ | 118 Hz |
| $2 \times 10^5$ | 61 |
| $1 \times 10^5$ | 30 |
| $5 \times 10^5$ | 14 |

Method for detection and determination of sample DNA

A sample DNA was isolated and purified by means of gel electrophoresis and the concentration of a solution was determined by measurement of absorbency at 260 nm and measurement of viscosity. A DNA to be immobilized was synthesized by the use of a DNA synthesizer (produced by Applied Biosystems Inc. and marketed under trademark designation of "DNA/RNA SYNTHESIZERS Type 392"). When necessary, the DNA thus synthesized, was amplified using a PCR device (produced by CETUS Corp.) using a thermostable DNA polymerase to about 100,000 times the original size prior to use.

Examples of DNA sequence (SEQ ID NOS. 1–4).
5'-GGTCATTAGTGGGCAGGCTCGTCT-3'—(A)
3'-CCAGTAATCACCCGTCCGAGCAGA-5'—(B)
5'-ACCTGGTAGCGTACCAAGCC-3'—(A)
3'-TGGACCATCGCATGGTTCGG-5'—(B)

EXAMPLE 2

A DNA sensor was manufactured by following the procedure of Example 1, except that a quartz oscillator 8 mm in diameter having a basic frequency of 9.95 MHz and provided with gold electrodes 3 mm in diameter was used instead.

In this example, the limit of DNA detection was about 300 molecules.

EXAMPLE 3

A DNA sensor was manufactured by following the procedure of Example 1, except that a quartz oscillator obtained by forming gold electrodes 1 mm in diameter on a quartz plate having a basic frequency of 20 MHz and measuring 4 mm in diameter was used instead.

In this example, the limit of DNA detection was 34 molecules of a sample DNA.

EXAMPLE 4

A DNA determination was carried out by following the procedure of Example 1, except that a DNA sensor was manufactured by forming gold electrodes 0.5 mm in diameter on a quartz plate having a basic frequency of 25 MHz and measuring 4 mm in diameter and the variation of resonance frequency was computed from the maximum frequency of conductance with the aid of an impedance analyzer (marketed under product code of "HP4194A") configured as illustrated in FIG. 4.

The mass sensitivity was 1.1 pg/Hz when the DNA was not immobilized. This fact indicates that the limit of DNA detection in this example was one molecule of the sample DNA.

It is clear from the foregoing description of the invention that the invention does not require any radioactive markers or radioactive enzymes and, therefore, allows the sample and other substances necessary for testing to be handled simply and safely. Further, the method of the present invention is also simple in operation. The determination contemplated by the present invention can be carried out quickly in comparison to conventional methods. In accordance with the present invention, knowledge of part of the sequence of a DNA to be detected is sufficient to allow for the detection of the DNA with several molecules being the limit of detection. Thus, it permits accurate detection of HIV virus, HCV virus, etc. on the gene level which should facilitate the diagnosis and therapy of diseases whose causes are on the gene level.

Since the method of this invention permits accurate and efficient detection of cancer genes and cancer repressing genes, it is capable of preventing return and crisis of the disease.

Further, because the detection part of the DNA sensor of the present invention can be regenerated, detection costs can be reduced by using this detection part repeatedly. Also, it is possible to conduct a plurality of DNA detections at the same time by forming a plurality of sequences on the DNA sensors in accordance with the present invention.

The mass grows because the QCE adsorbs nonspecific chemical species (DNA's other than the DNA being tested for and proteins, for example). The present invention comprises a method resorting conversely to the decrease of mass, produces a reverse action to that of the nonspecific chemical species, and therefore permits accurate detection of the DNA being detected, and also provides for high selectivity (specificity).

When minute magnetic particles are used as a high-mass chemical species, for example, the method of the present invention is advantageous in the fact that it enables the sensor to be regenerated by recovering the released DNA (B) chains, e.g. with an electromagnet and hybridizing the recovered DNA (B) chains with the DNA (A) chains immobilized on the sensor.

The base sequence reading device of the present invention is provided with an integrated alley of nucleotide chains which are intended for sequencing, means for measuring variations of characteristics caused in an electromechanical conversion element when the integrated alley is hybridized with a gene intended for detection, and means for analyzing the data obtained by the measurement and consequently allowing for the accurate reading of the base sequence of the gene of interest.

The present invention deciphers the base sequence of a gene given for the purpose of analysis by the use of a sensor which is provided with a quartz oscillator having all the sequences of nucleotide chains two-dimensionally disposed on one of the opposite surfaces of the quartz oscillator, with addresses assigned to the sites of disposition of the series, and having minute gold electrodes formed on the other surface at the positions corresponding to the sites of nucleotide chains, minute probes for electric connection to the minute electrodes, a scanner part for switching the outputs from the minute probes, means for measuring impedance of each of the minute electrodes, means for hybridizing the quartz oscillator having all the sequences of nucleotide chains fixed thereon with the gene intended for analysis, then analyzing the results of measurement of impedance by accurately measuring variations of impedance at the parts of the quartz oscillator corresponding to the addresses mentioned above, and consequently computing variations of the parameter and resonance frequency of an equivalent circuit, means for detecting the addresses of sequence having positively shifted resonance frequency and memorizing and recording the size of frequency shift, the parameter of equivalent parameter, etc., means for reading the relevant base sequence from the table of correspondence of the addresses of disposition to the base sequence of immobilized nucleotide chains, and means for tying all the information on the hybridized and immobilized base sequences of nucleotide chains without contradiction.

Nucleotide chains having a chain length of at least 7 can be hybridized with a gene subjected to detection with high selectivity. However, there is no particular upper limit for their chain length. For example, the whole library of sequences is disposed on an electromechanical conversion element and the nucleotide chains to be used therein have one equal chain length, the upper limit is desired to be about 20 in the light of the fact that the number of combinations of nucleotide chains increases logarithmically for each increase of one nucleotide. The chain length may be 100 or even more where the nucleotide chain happens to be a fragment of the base sequence expected to be possessed by the gene subjected to detection.

Desirably, the gene detecting part of the present invention is composed of an elastic wave element and another nucleotide chain having the same nucleic acid sequence as the gene which is being detected. Further, a chemical species having a larger mass than the mass of the gene subjected to detection is immobilized to the nucleotide chain immobilized on the surface of the electrode of the elastic wave element and to the other nucleotide chain which is complementarily bound to the nucleotide mentioned above.

For example, an octamer DNA immobilizing element has either of the opposite 5'-terminals of a nucleotide chain immobilized to the surface of an electrode of the elastic wave element and has a chemical species immobilized to the other 5'-terminal of the nucleotide chain hybridized to the nucleotide chain on the opposite side. This element can read the whole base sequence of a DNA subjected to detection by detecting an increase of the oscillation frequency due to a decrease of mass resulting from complementary exchange bonding with the DNA and consequently detecting an octal base sequence in the DNA.

The term "electromechanical conversion element" as used in this invention refers to an element which is possessed of an electric-mechanical conversion function or an electric-mechanical-optical conversion function and the term "elastic wave element" refers to an electric-acoustic transducer. A quartz oscillator, a surface elastic wave element, and bulk elastic wave element are specific examples thereof.

The operation of the base sequence reading device of this invention has been described in detail. The gene detecting part of the device has been also described above.

Now, the base sequence reading device of this invention will be described more specifically below with reference to the accompanying drawings.

Figure 7:
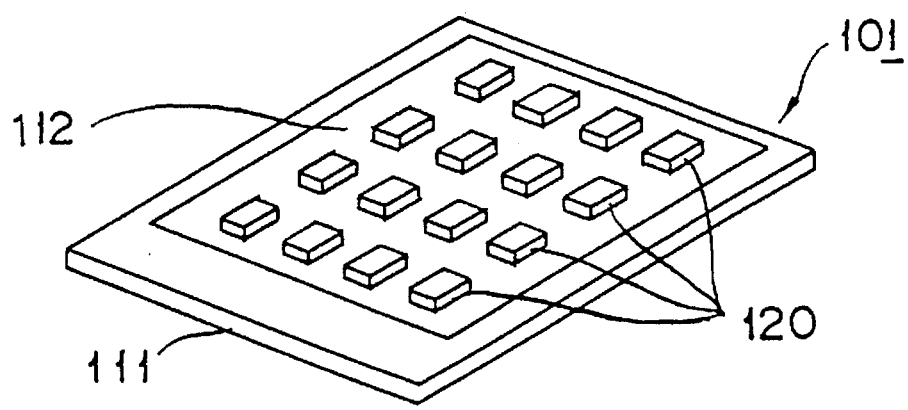
FIG. 7 is a model diagram illustrating the appearance of a gene detecting part, intended to aid in the explanation of the principle of detection of a base sequence according with this invention.

FIG. 7 is a model diagram illustrating the appearance of the gene detecting part. On the surface of a quartz oscillator 101, 256×256 octamer nucleotides 120 are two-dimensionally arranged and identified with addresses. The addresses assigned to the two-dimensional sites are so arranged under a fixed rule as to facilitate location of the base sequence of the octamer. Binary notation, for example, enables these addresses to be conveniently processed with a computer. The binary notation is allotted to the base respectively such that adenine (A)→"00", cytosine (C)→"01", guanine (G)→"10" and thymine (T)→"11". 8 Base can be expressed as binary notation of 16 bit length. If upper and lower 8 bits are respectively converted to decimal rotation, they correspond to x and y of two-dimensional arrangement (x, y). Base sequence of the octamer can easily be read from the addresses assigned to the two-dimensional sites. For example, base sequence of AAAAAAAA can be expressed by "0000000000000000" and fixed at (0, 0), base sequence of CCCCCCCC can be expressed by "0101010101010101" and fixed at (85, 85), and base sequence of TTTTTTTT can be expressed by "1111111111111111" and fixed at (255, 255). By contrast, when the base sequence is read from the address, it can be determined by factors x and y of the address (x, y) converted to binary notation and tied, and then converted to base sequence from upper portion to each two bits. To the individual immobilized octamer nucleotides, an octamer nucleotide having minute particles bound chemically thereto is complementarily bound. As the minute particles, minute polymer particles such as polystyrene beads and minute ceramic particles such as ferrite which have an average mass of 0.1 pg may be used.

Figure 8:
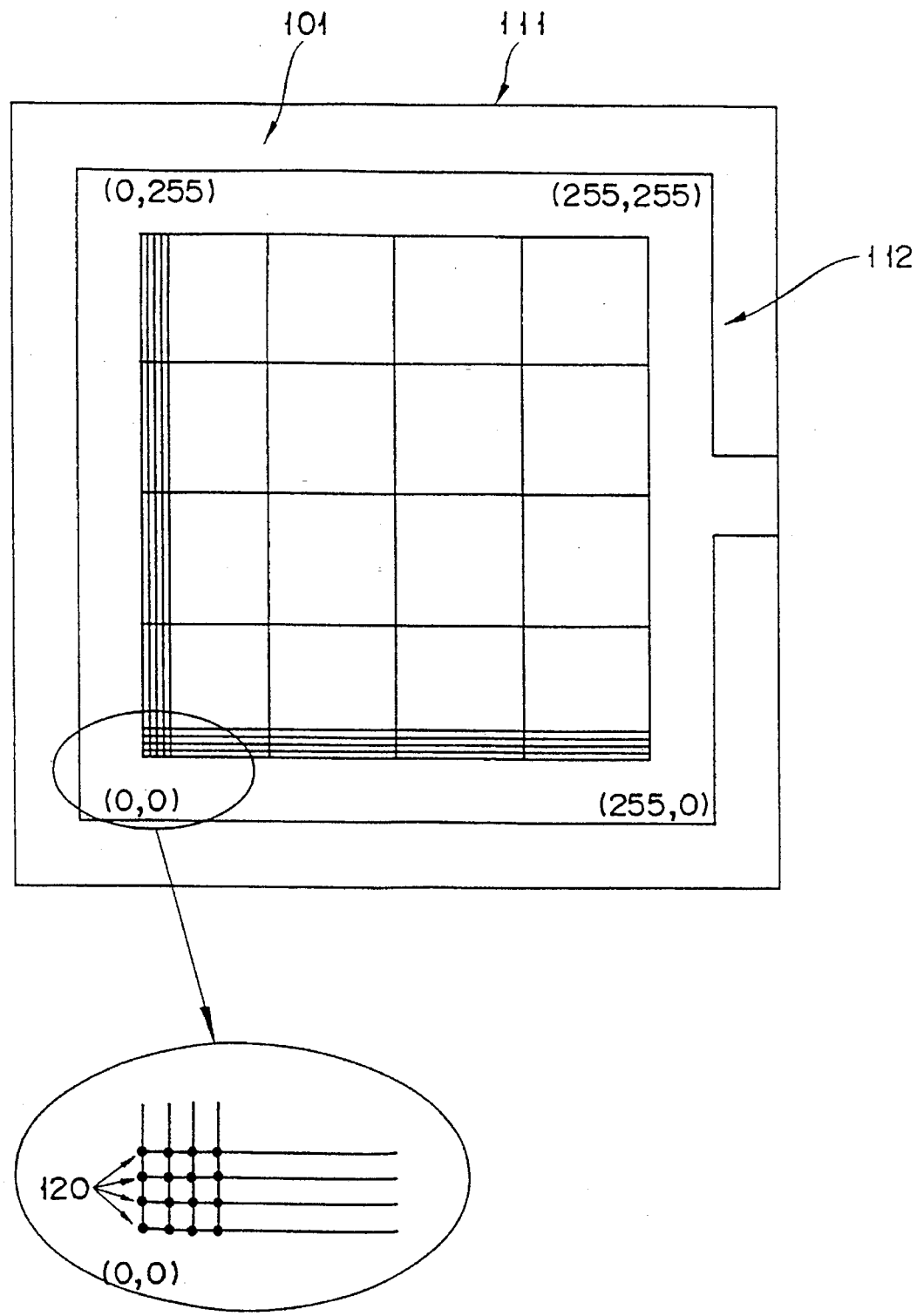
FIG. 8 is a surface diagram of an octamer immobilizing element for portraying the two-dimensional sequence of an octamer.

A diagram depicting the surface of the octamer immobilizing element having octamers two-dimensionally arranged thereon is given in FIG. 8.

Figure 9A:
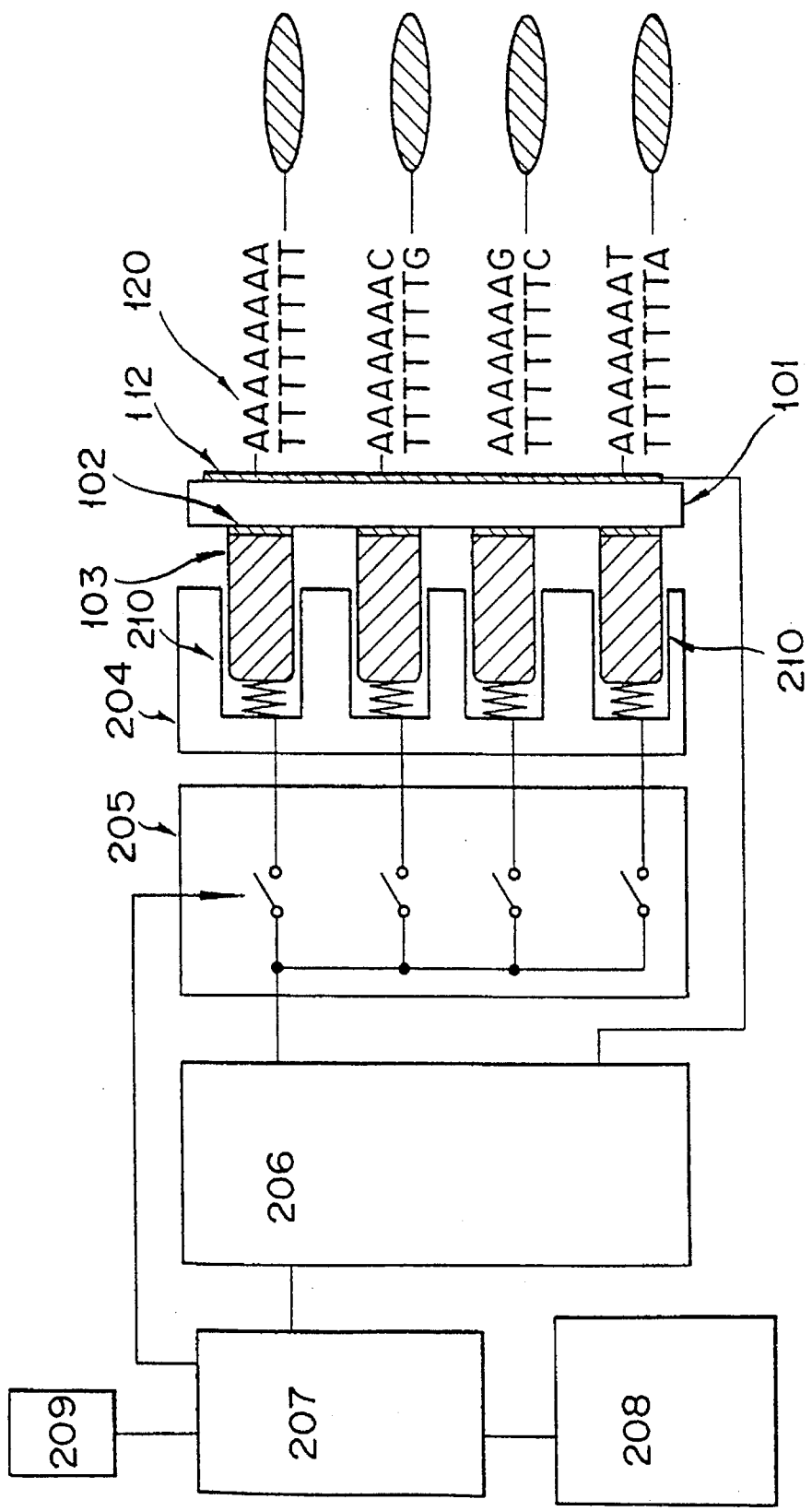
FIG. 9(A) is a block diagram illustrating an embodiment of the DNA reading device of this invention.

FIG. 9(A) is a block diagram illustrating an embodiment the DNA reading device of this invention. On the surface of the quartz oscillator opposite to the surface thereof having all the octamer sequences are immobilized, 50×50 μm² minute gold electrodes are formed at positions corresponding to those at which the octamers are immobilized. The gene detecting part is connected electrically to the individual minute electrodes through the medium of minute probes. The outputs from the electrodes are switched by a scanner 205 illustrated in FIG. 10 and applied to an impedance measuring device.

The minute probes 203 are attached to a prober device 204 provided with a mechanism adapted to generate a three-dimensional motion and are caused to move so as to contact the part of all the sequences.

The quartz oscillator 201 having all the octamer sequences immobilized thereon, after being hybridized with the DNA subjected to analysis, accurately measures and analyzes a variation of the quartz oscillator in the parts corresponding to the addresses with the aid of an impedance measuring device 206 and calculates the parameter of an equivalent circuit and the variation of the resonance frequency. It then detects the address of a sequence which has produced a shift of the resonance frequency and memorizes and records the size of the frequency shift, the parameter of the equivalent circuit, etc. It then reads the base sequence of eight bases from the table of correspondence between the addresses of sites and the immobilized DNA base sequences.

Then, based on the information on all the octal base sequences obtained as described above, the base sequence of the DNA subjected to analysis can be deciphered.

The flow chart of the operation described thus far is shown in FIGS. 11(A) to (D). The hybridization illustrated in FIG. 11(B) in the same as that shown in FIG. 5 (B).

The principle by which the present invention provides for DNA detection is further described below. Essentially, the difference of variation of mass which is generated when the gene DNA subjected to detection is homologously displaced by the modified DNA having a homologous sequence with the DNA immobilized to the sensor is measured in the form of a variation of the oscillation of the elastic wave element with high sensitivity. When the DNA destined to be displaced is given a mass greater than that of the DNA subjected to detection, the detection and identification of the gene can be attained quickly, even at the level of a single DNA. The minute particles of high-mass chemical species which are bound to the DNA (B) chain destined to be displaced are released at the same time that the displacement is effected. Therefore, allowing y to stand for the mass of the DNA (B) chain being detected, a for the mass of the minute particles of chemical species, and x for the mass of the immobilized DNA (B) chain and assuming that the mass of the minute particles is greater than that of the DNA (B) chain being detected, the relation of a>>y>x will be established. Thus, the variation of the mass can be expressed as follows.

$$\Delta ma = y - x - a (\Delta ma < 0)$$

In the absence of the minute particles of chemical species, the variation of mass may be expressed as follows.

$\Delta m = y - x (\Delta m > 0)$

Thus, the variation is reversed (in the direction of decreasing mass) and the variation of mass is amplified to ($|\Delta ma/\Delta m|$) times the original value with the homologous exchange reaction as a trigger.

In this invention $y \leq 5 \times 10^{-17}$ (g) holds because the maximum length of DNA subjected to detection is fixed at 100 kbp and $x = 4 \times 10^{-20}$ (g) holds because the immobilized DNA is an octamer. It is concluded, therefore, that the amplification is attained to not less than $10^4$ times the original value provided that the mass of the minute particles is 0.1 pg.

The mass sensitivity is calculated as follows.

The mass sensitivity of an AT cut quartz oscillator [$\Delta m/ \Delta$, (g/Hz)] is expressed by the following formula.

$\Delta m/\Delta F = -4.348 \times 10^{-7} A (F_0)^{-2}$ (1) wherein $F_0$ is resonance frequency (MHz) and A is surface area of electrode (cm$^2$). The mass sensitivity of the electrode part of an area of 50×50 μm$^2$ on the AT quartz oscillator having $F_0 = 10$ MHz, therefore, is found to be roughly 0.1 pg/Hz.

Thus, based on the foregoing, the minimum detection level provided by the subject method is one molecule of DNA when the sensor is designed so as to produce a variation of mass of 0.1 pg.

EXAMPLE 5 (SCANNER VERSION)

Now, a working example of this invention will be described specifically below with reference to the accompanying drawings.

FIG. 9(A) is a block diagram illustrating a DNA reading device which is one embodiment of this invention. This DNA reading device is composed of (1) an octamer-immobilized quartz oscillator 101 having octamer nucleotides of all the possible combinations of base sequences immobilized on a quartz oscillator, (2) a probe device 204 provided with minute probes 103 intended to be connected to minute electrode parts 102 formed correspondingly to an octamer immobilizing pattern, (3) a scanner 205 adapted to switch the electrode parts 102, (4) an impedance analyzer 206 for measuring variations of the resonance frequency and the resistance component of the quartz oscillator, (5) a data processing device for analyzing the frequency data consequently 207 obtained and detecting a variation of the frequency, (6) an octamer library 208 of 8 mer, and (7) a set of software 209 for analyzing the DNA sequence based on the variation of frequency.

The octamer-immobilized quartz oscillator 101 has 256× 256 octamer nucleotides 120 of base sequences two-dimensionally arrayed on the surfaces of gold electrodes 112 on a quartz oscillator (the square of 20 mm) having a basic resonance frequency of 10.6 MHz as shown in FIG. 8. The two-dimensional arrangement is effected under a fixed rule so as to facilitate correlation with the octamer base sequences. To the individual immobilized octamer nucleotides are hybridized octamer nucleotides which have minute particles immobilized thereon. As the minute particles, polystyrene beads having an average mass of 0.1 pg are used.

On the opposite surface of the octamer-immobilized quartz oscillator 101, minute electrode parts 102 of thin gold film 50 μm in diameter are formed at the positions corresponding to the sites of immobilization of the octamers. The quartz oscillator 101 is electrically connected to the minute electrode parts through the medium of minute probes 103. The outputs from the minute electrode parts are switched by the scanner 205 and then applied to the impedance measuring device. The minute probes are incorporated in the probe device which is fitted with a mechanism capable of producing a three-dimensional motion of a probe head 210 formed by bundling 2 to 128 of the minute probes.

EXAMPLE 6

Figure 9B:
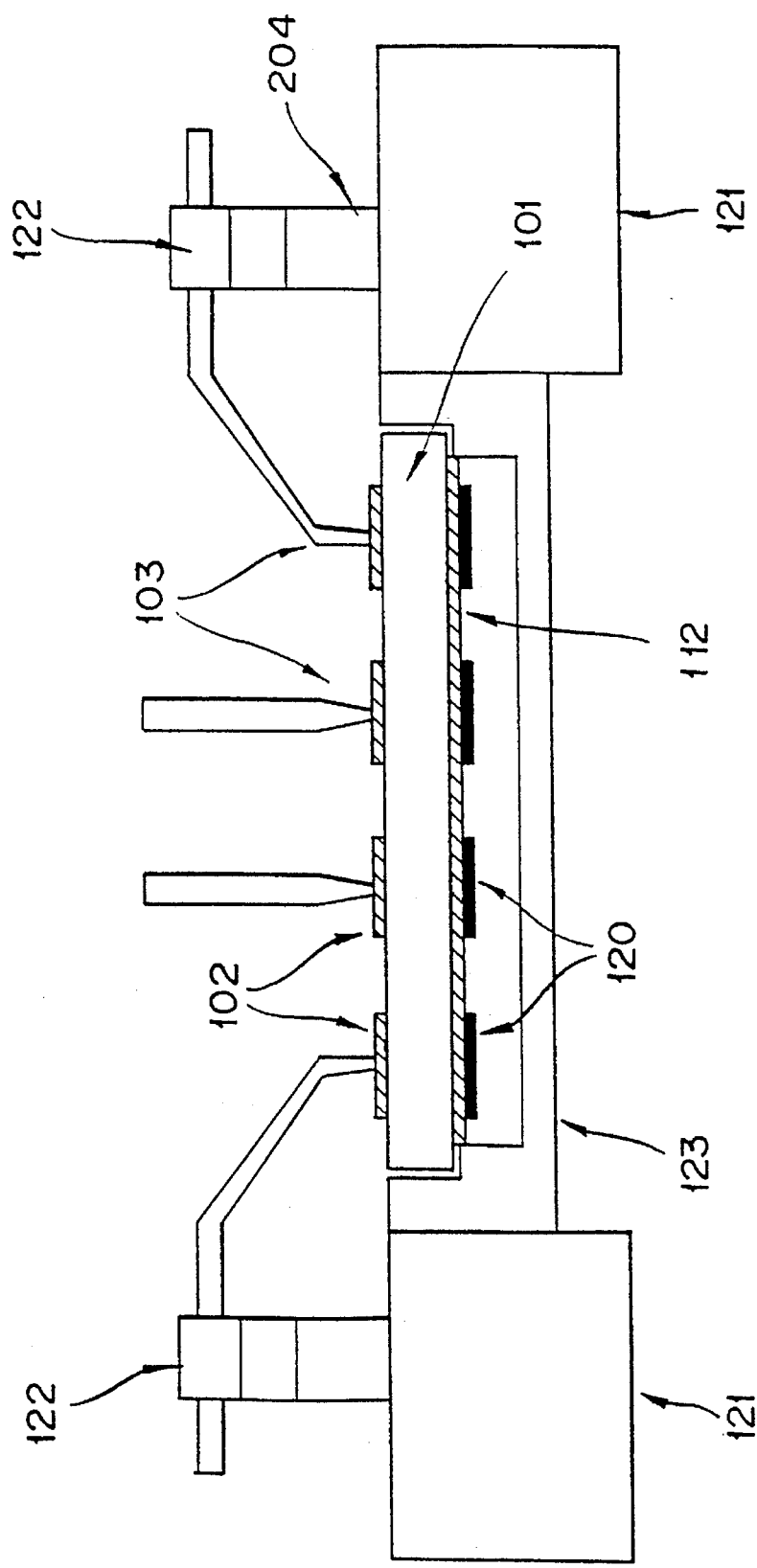
FIG. 9(B) is a concept illustrating an embodiment of a probe device.
Figure 11A:
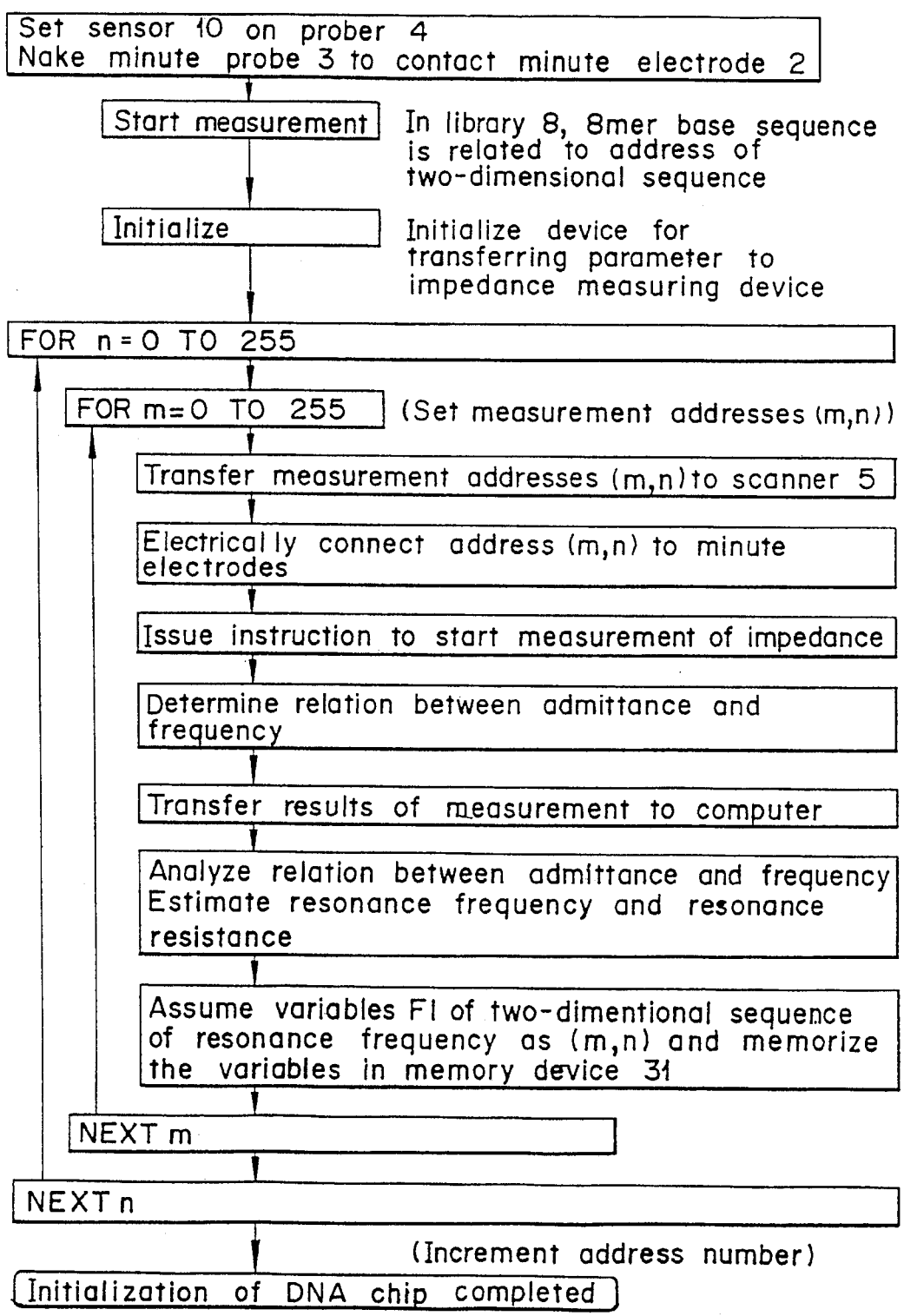
Figure 11D:
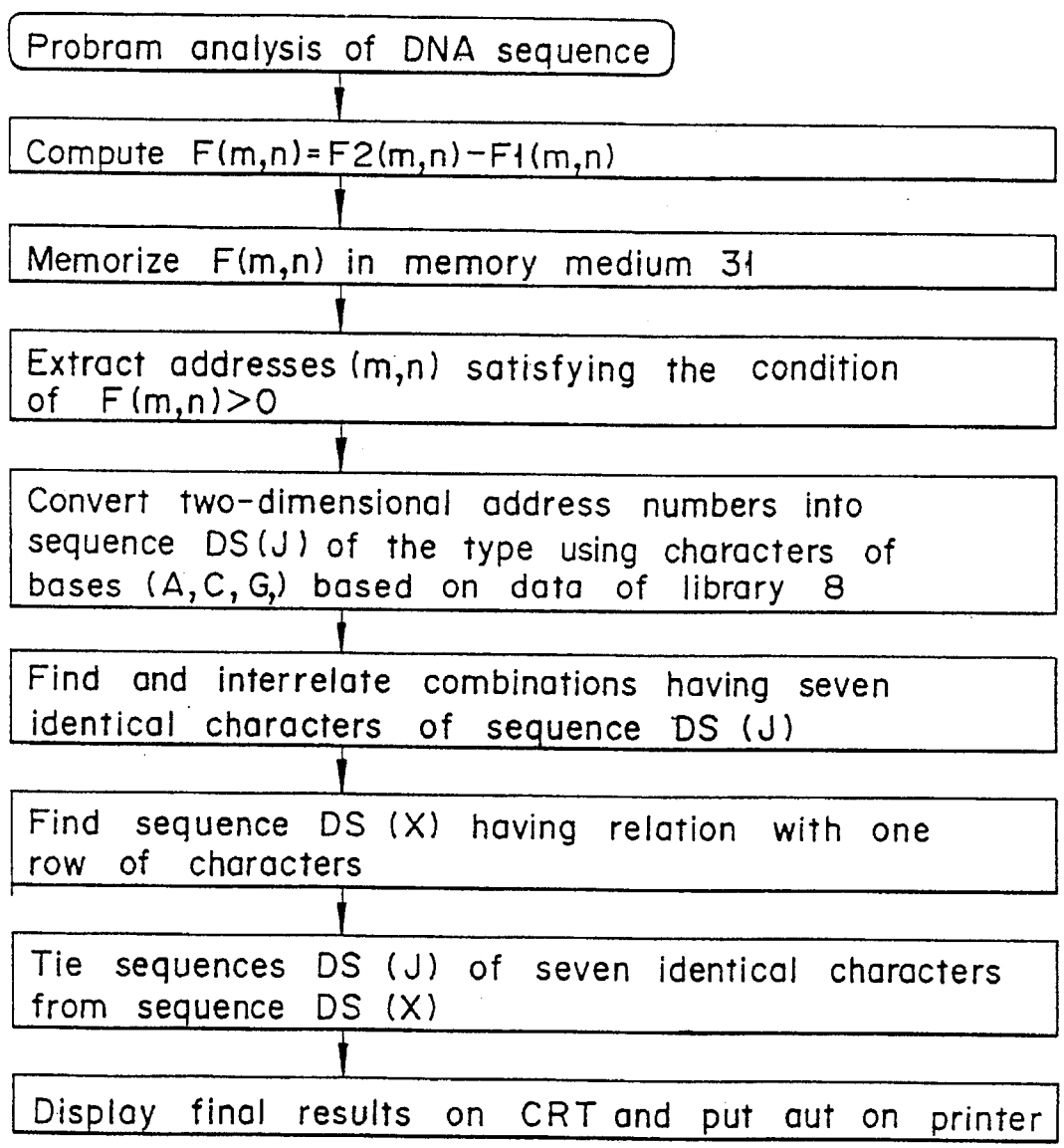

In another embodiment, a probe device 204 provided minute probes 103 to xyz manipulator 122 as shown in FIG. 9 (B) can be used as a probe device 204 for connecting with a minute electrode parts 102.

EXAMPLE 7

In still another embodiment, a position of a minute probe 103 is transferred and scanned to a minute electrode 102 by controlling xyz manipulator of the probe device from a computer 207 without using the scanner 205 as shown in FIGS. 9 (A) and 9(C).

By the use of the gene reading device which is constructed as described above, DNA's (Formula 2: SEQ ID NO. 5) of 20 bases of a known sequence were synthesized and subjected to test. Formula 3 (SEQ ID NO. 6) represents a nucleotide chain complementarily bound to that of Formula 2 (SEQ ID NO. 5). In the formula, (x, y) is addressed.

5'-GGATCGATCCAATCGTACTG-3'(2)
3'-CCTAGCTAGGTTAGCATGAC-5'(3)

It is from FIG. 12 which illustrates the results of reading that the DNA's were hybridized with 26 immobilized octamers. When the numbers 1 to 26 were assigned to the 26 octamer sequences and pairs sharing an equal sequence of seven bases were sought out and orderly arranged, the sequences of 1 to 13 read as (SEQ ID NO. 5) GGATCGATCCAATCG-TACTG. It was further found that the sequences of 14 to 26 read as (SEQ ID NO. 6) CCTAGCTAGGTTAGCATGAC. The sequences thus deciphered were respectively homologous with those of Formula 2 and Formula 3. It is clear from the description given thus far that the use of the device of this invention permits various sequences of genes to be read.

What is claimed is:

1. A method for detecting a target DNA in a sample comprising the following steps:
   (i) immobilizing a double stranded nucleic acid sequence to the surface of an electrode of an elastic wave element, wherein said double stranded nucleic acid sequence comprises a first nucleic acid sequence having a 5'-terminus which is bound to the surface of the electrode of the elastic wave element, and a second nucleic acid sequence which is complementary to the first nucleic acid sequence which is hybridized to the first sequence and wherein the 5'-terminus of said second nucleic acid sequence is bound to a chemical species of sufficient molecular weight to produce a nucleic acid sequence having a higher mass than a target DNA which is to be detected;
   (ii) contacting said immobilized nucleic acid sequence with a sample suspected of containing a target DNA sequence which is complementary to the first nucleic acid sequence under conditions that provide for the displacement of the second nucleic acid sequence from the first nucleic acid sequence and the hybridization of the target DNA sequence to the first nucleic acid sequence; and
   (iii) detecting the presence of the target DNA sequence in the sample on the basis of an increase in oscillation frequency caused by the reduction in mass of the immobilized double stranded nucleic acid sequence which occurs upon displacement of the second nucleic acid sequence by the target DNA sequence and the subsequent hybridization of the target DNA to the first DNA sequence.

2. A method according to claim 1, wherein said elastic wave element is a quartz oscillator or a surface elastic wave element.

3. A method according to claim 1, wherein said chemical species has mass in the range of 0.01 pg to 1 ng.

4. A method according to claim 1, wherein said chemical species has a specific gravity of not less than 1 $g/cm^3$.

5. A method according to claim 1, wherein said chemical species has a diameter in the range of 0.01 to 10 μm.

6. A method according to claim 1, wherein said chemical species is at least one member selected from the group consisting of synthetic resins, magnetic materials, metals, and metal oxides.

7. A method according to claim 6, wherein said synthetic resin is polystyrene of fluorine resin.

8. A method according to claim 6, wherein said metal is gold or said metal oxide is titanium oxide.

9. A method according to claim 6, wherein said magnetic material is a ferrite.

10. A DNA sensor which provides for the detection of a target DNA sequence comprising a double stranded nucleic acid sequence which is immobilized to the surface of an electrode of an elastic wave element, wherein said double stranded nucleic acid sequence comprises a first nucleic acid sequence having a 5'-terminus which is bound to the surface of the elastic wave element, and a second nucleic acid sequence complementary thereto, which is not said target DNA sequence and which is hybridized to the first nucleic acid sequence and wherein the 5' terminal end of said second nucleic acid sequence is bound to a chemical species of sufficient molecular weight to produce a nucleic acid sequence having a greater mass than a target DNA complementary to the first DNA sequence which is to be detected on the basis of increased oscillation frequency.

11. A DNA sensor according to claim 10, wherein said elastic wave element is a quartz oscillator or a surface elastic wave element.

12. A DNA sensor according to claim 10, wherein said chemical species has a mass in the range of 0.01 pg to 1 ng.

13. A DNA sensor according to claim 10, wherein said chemical species has a specific gravity of not less than 1 $g/cm^3$.

14. A DNA sensor according to claim 10, wherein said chemical species has a diameter in the range of 0.01 to 10 μm.

15. A DNA sensor according to claim 10, wherein said chemical species is at least one member selected from the group consisting of synthetic resins, magnetic materials, metals, and metal oxides.

16. A DNA sensor according to claim 15, wherein said synthetic resin is polystyrene or fluorine resin.

17. A DNA sensor according to claim 15, wherein said metal is gold or said metal oxide is titanium oxide.

18. A DNA sensor according to claim 15, wherein said magnetic material is a ferrite.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
( A ) LENGTH: 24 base pairs
( B ) TYPE: nucleic acid
( C ) STRANDEDNESS: single ( D ) TOPOLOGY: linear ( i i ) MOLECULE TYPE: DNA (genomic)

( x i ) SEQUENCE DESCRIPTION: SEQ ID NO:1:

GGTCATTAGT GGGCAGGCTC GTCT 24

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

CCAGTAATCA CCCGTCCGAG CAGA 24

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

ACCTGGTAGC GTACCAAGCC 20

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

TGGACCATCG CATGGTTCGG 20

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

GGATCGATCC AATCGTACTG 20

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

CCTAGCTAGG TTAGCATGAC 20

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

CCGAGCTAGG TTAGCATGAC 20

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

GTCATGCTAA CCTAGCTAGG 20

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

CAGTACGATT GGATCGAGCC 20